United States Patent [19]

Glazier

[11] Patent Number: 5,789,589
[45] Date of Patent: Aug. 4, 1998

[54] GUANINE ANALOG PHOSPHATES

[75] Inventor: Arnold Glazier, Newton, Mass.

[73] Assignee: Drug Innovation & Design, Inc., Needham, Mass.

[21] Appl. No.: 635,553

[22] Filed: Apr. 22, 1996

[51] Int. Cl.⁶ .......................... C07D 473/18; C07F 9/6561
[52] U.S. Cl. ................... 544/244; 544/243; 544/276; 544/277
[58] Field of Search ........................... 544/243, 244, 544/276, 277

[56] References Cited

U.S. PATENT DOCUMENTS

| | | | |
|---|---|---|---|
| 4,146,715 | 3/1979 | Schaffer | 544/276 |
| 4,294,831 | 10/1981 | Schaeffer | 544/277 |
| 4,806,642 | 2/1989 | Sircar et al. | 544/244 |
| 4,816,447 | 3/1989 | Ashton et al. | 544/244 |
| 4,845,084 | 7/1989 | Hannah et al. | 544/244 |
| 5,055,458 | 10/1991 | Bailey et al. | 514/81 |

FOREIGN PATENT DOCUMENTS 0143987  10/1984  European Pat. Off. .
WO90/08128  7/1990  WIPO .
WO96/40088  12/1996  WIPO .

*Primary Examiner*—Mukund J. Shah
*Assistant Examiner*—Pavanaram K. Sripada
*Attorney, Agent, or Firm*—Hamilton, Brook, Smith & Reynolds, P.C.

[57] ABSTRACT

Disclosed are novel prodrugs represented by the following structural formulas:

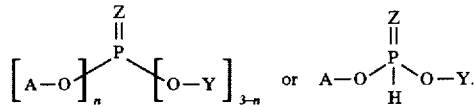

Z is oxygen or sulfur; n is 1 or 2; Y is, together with a hydroxy group, acyclovir or an analog of acyclovir; A is a group which can be metabolized in vivo to a give a modified A such that the phosphoester bond (modified A)—O undergoes cleavage in vivo. Also disclosed is a method of treating a viral infection in an individual or animal. The method comprises administering to the individual or animal a therapeutically effective amount of a prodrug represented by structural formula shown above.

16 Claims, No Drawings

GUANINE ANALOG PHOSPHATES

BACKGROUND

Antiviral agents currently in use are of limited effectiveness in treating dermal infections caused by viruses. For example, herpes simplex labialis, commonly referred to as "cold sores" do not respond to the topical treatment with acyclovir (Spruance et al., *Am. J. Med.*, 73(1A):315–319 (1982); Shaw et al., *Br. Med. J. (Clin. Res. Ed.)*, 291(6487) :7–9 (1985); Raborn, et al., *Oral Surg. Oral Med. Oral Pathol.*, 67(6):676–679 (1989); Spruance, et al., *Antimicrob. Agents Chemother.*, 25(5):553–555 (1984); Raborn, et al., *J. Can. Dent. Assoc.*, 55(2):135–137 (1989)). Oral administration of acyclovir for the treatment of cold sores is only partially effective (Spruance et al., *J. Infect. Diseases* 161:185 (1990)).

The limited effectiveness of antiviral agents such as acyclovir applied topically to cold sores and other dermal viral infections is thought to be a consequence of the limited ability of most of these agents to penetrate the skin (Parry, et al., *J. Invest. Dermatol.*, 98(6):856–863 (1992); Spruance, et al., *Antimicrob. Agents Chemother.*, 25(1):10–15 (1984)). Topical treatments for genital herpes infections are also ineffective for the same reason. Consequently, there is a need for new antiviral agents which can penetrate the skin and which are active against viruses which cause dermal infections.

SUMMARY OF THE INVENTION

The present invention is directed to a novel class of prodrugs which can be metabolized to acyclovir monophosphate or analogs of acyclovir monophosphate in vivo and to methods of treating viral infections with these novel prodrugs. It has now been found that the prodrugs disclosed herein are more effective in treating certain viral infections than acyclovir. Treatment of guinea pigs suffering from dermal herpes simplex virus-1 (HSV-1) lesions with Prodrug 1 or Prodrug 2 resulted in a dramatic reduction in lesion number,

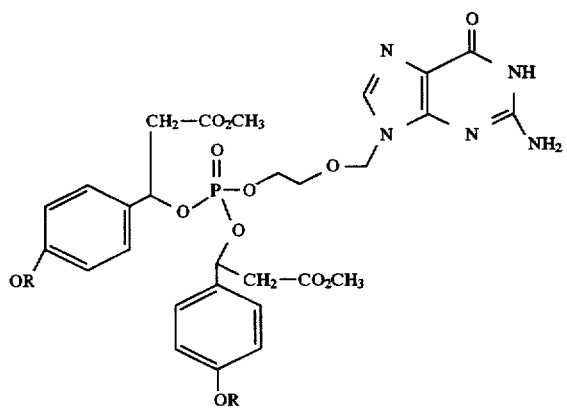

1) R = —CO—CH₃ (Ac)
2) R = —CO—C(CH₃)₃ in lesion area and in lesion virus titer (Example 1) when compared to its vehicle. In contrast, comparable treatment with U.S. ZOVIRAX (acyclovir) resulted in a statistically insignificant reduction in total lesion area and a reduction in lesion virus titer that was significantly less than observed with Prodrugs 1 or 2. Prodrugs 1 and 2 were also about 2× and about 5×, respectively, more active in vitro against acyclovir resistant strains of HSV-1 than acyclovir (Example 2). Topical application of Prodrug 2 is also effective in promoting the healing of vaginal lesions in mice caused by Herpes Simplex Virus-1.

In one embodiment the present invention is a prodrug of acyclovir monophosphate or an acyclovir monophosphate analog. The prodrug is represented by Structural Formula (I) or Structural Formula (II):

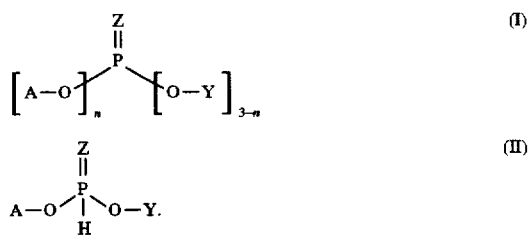

Z is oxygen or sulfur, preferably oxygen.

n is 1 or 2.

Y is, together with a hydroxy group, acyclovir or an analog of acyclovir.

A is a group which can be metabolized in vivo to give a modified A (or A') such that the phosphoester bond (modified A)—O undergoes cleavage in vivo.

Another embodiment of the present invention is a method of treating a viral infection in an individual or animal. The method comprises administering to the individual or animal a therapeutically effective amount of a prodrug represented by Structural Formula (I) or (II).

DETAILED DESCRIPTION OF THE INVENTION

Disclosed herein is a method of increasing the effectiveness of antiviral drugs such as acyclovir which are nucleotide analogs. The effectiveness of antiviral agents such as acyclovir and acyclovir analogs can be enhanced by converting the agent into a phosphorus containing prodrug represented by Structural Formula (I) or (II). Phosphorus containing prodrugs are described in U.S. Ser. Nos. 07/714, 130, 07/537,332 and 08/310,972, the entire teachings of which are hereby incorporated into this application by reference.

A prodrug, as used herein, is an agent which can be metabolized in vivo, i.e. undergoes biotransformation, to give the pharmacologically active agent or a monophosphate of the pharmacologically active agent. "Metabolized" refers to chemical or biochemical reactions which the prodrug undergoes in vivo. Examples include enzyme catalyzed reactions and reactions which occur in solution such as solvolysis and hydrolysis.

Use of a prodrug for treating an individual can have advantages over the parent drug, e.g. greater lipophilicity to enhance delivery of the pharmacologically active agent across cell membranes or into the stratum corneum of the skin. Accordingly, lipid solubility is a desirable property for antiviral drugs. The prodrugs of the present invention are lipophilic enough to penetrate into the stratum corneum of the skin and are uncharged molecules which can be transformed in vivo into acyclovir, an analog of acyclovir, acyclovir monophosphate or an analog of acyclovir monophosphate.

As used herein, an "acyclovir analog" is a purine with a C3 to about a C12 substituted alkyl group bonded to nitrogen nine. As used herein, a "purine" has a pyrimidine ring fused to an imidazole ring. It will be understood that tautomeric forms of a purine are also included, such as in the structure shown for Prodrugs 1 and 2.

The carbon atoms of the purine can be bonded to or substituted by, for example, a hydrogen, halogen, hydroxy, (lower alkyl)—O—, thio, (lower alkyl)thio, amino, (lower alkyl)amino, di(lower alkyl)amino, (lower alkyl)—CO—NH— or azide.

The alkyl or substituted alkyl group bonded to nitrogen nine of the purine (nitrogen nine is indicated in Structural Formula (III)) can optionally have an ether, thioether or amine moiety linkage within the chain and is straight chained or branched. The substituted alkyl group can have one or more substituents, such as halogen, hydroxy, amino, —NH(lower alkyl), (lower alkyl)—O—, (substituted lower alkyl)—O—, aryl, substituted aryl, aryloxy, substituted aryloxy, (lower alkyl)NH—$SO_2$—O—, (substituted lower alkyl) NH—$SO_2$—O—, (aryl) NH—$SO_2$—O—, (substituted aryl) NH—$SO_2$—O—, phosphate, —NH—CO-(lower alkyl), —NH—CO-(substituted lower alkyl), —NH—CO-aryl, —NH—CO-(substituted aryl), (lower alkyl)—CO—, (substituted lower alkyl)—CO—, —CO-aryl and —CO-(substituted aryl). Lower alkyl, substituted lower alkyl, aryl and substituted aryl are defined hereinbelow.

In a preferred embodiment, an "acyclovir analog" is represented by Structural Formula (III):

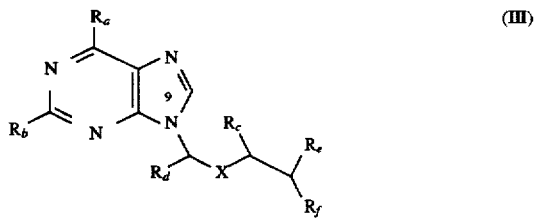

(III)

X is sulphur, nitrogen or oxygen.

$R_a$ is hydrogen, halogen, hydroxy, (lower alkyl)—O—, azide, thio, (lower alkyl)thio, amino, (lower alkyl) amino or di(lower alkyl)amino.

$R_b$ is hydrogen, halogen, (lower alkyl)thio, (lower alkyl) —CO—NH— (referred to herein as "acylamino"), amino or azide.

$R_c$ is hydrogen, lower alkyl, substituted lower alkyl, aryl, substituted aryl. Aryl is preferably phenyl.

$R_d$ is hydrogen, lower alkyl and substituted lower alkyl.

$R_e$ is hydrogen, lower alkyl, substituted lower alkyl, aryl, substituted aryl, (lower alkyl)O—, (substituted lower alkyl)O—, aryloxy and substituted aryloxy.

$R_f$ is hydroxy.

In a preferred embodiment, Y is represented by Structural Formula (IV):

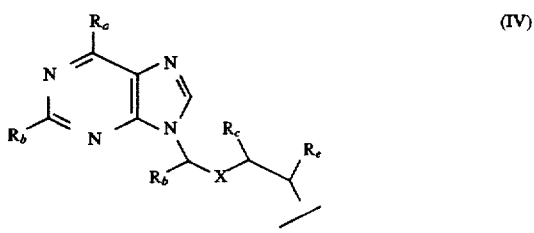

(IV)

As seen from Structural Formula (IV), when acyclovir or an acyclovir analog is used to form a prodrug of the present invention, $R_f$ in Structural Formula (III) is a covalent bond between acyclovir or the acyclovir analog and an oxygen bonded to a phosphorus atom of the prodrug. For example, in Structural Formula (I) or (II) $R_f$ is a covalent bond between Y and an oxygen bonded to phosphorus, referred to herein as a "phosphoester bond". The covalent bond between A and O is also a phosphoester bond.

Specific examples of suitable acyclovir analogs are provided in U.S. Pat. Nos. 4,199,574, 4,294,831 and 4,323,573, the entire teachings of which are hereby incorporated into this patent application by reference.

In a preferred embodiment, $R_a$ is —OH, $R_b$ is —$NH_2$ and X is oxygen. It is most preferred that $R_c$, $R_d$, and $R_e$ are each —H and $R_f$ is a phosphoester bond between Y and an oxygen of the phosphate of the prodrug, i.e. Y, together with a hydroxy group, is acyclovir.

The following is a description of the present invention with respect to prodrugs comprising phosphate groups, e.g., prodrugs represented by Structural Formula (I). It is to be understood that the following discussion applies to other prodrugs encompassed by the present invention, e.g., prodrugs represented by Structural Formula (II).

A is a group which can be metabolized in vivo to give a chemically modified A (A'). As a result of the biotransformation, the phosphoester of the prodrug which comprises modified A (A') undergoes cleavage in vivo. Cleavage of the phosphoester can result, for example, from the heterolytic cleavage of the oxygen-carbon bond of the phosphoester group comprising a modified A (A'). In this instance, the phosphate acts as a leaving group. Cleavage in vivo of a phosphoester comprising modified A (A') will be enhanced relative to a phosphoester comprising A if biotransformation in vivo results in a greater electron density on the carbon atom to which the phosphate is bonded in modified A (A') than on the carbon atom to which the phosphate is bonded in A.

For example, a compound having a structure represented by Structural Formula (I) or (II) will be cleaved more rapidly in vivo when A is a benzyl with an electron donating group in the ortho or para position than when A is an unsubstituted benzyl group. Thus, A can be, for example, a benzyl group that undergoes biotransformation in vivo such that electron donating groups are introduced at the ortho and/or para positions, or such that groups already present at the ortho and/or para positions are converted into groups that are more strongly electron donating in modified A (A') than in A.

Protected hydroxy groups such as acyloxy groups (e.g., lower alkyl—CO—O— and aryl—CO—O—), carbonate groups (e.g., —O—CO—O-lower alkyl and —O—CO—O-aryl), carbamate groups (e.g., —O—CO—NH-lower alkyl and —O—CO—NH-aryl) and protected aryl amine groups such as acylamine groups (e.g., lower alkyl—CO—NH— and aryl—CO—NH—) are only very slightly electron donating, but can be converted (e.g. unmasked) in vivo into the strongly electron donating hydroxy or amino groups, respectively. For example the Hammett para sigma+constant for the acetoxy group and the acetyl amino group are –0.06 are –0.60, respectively. In contrast, the hydroxy group and the amino group are strongly electron donating. The Hammett sigma para+constant for the hydroxy and amino groups are –0.92 and –1.7, respectively. The ionized hydroxy group (—O) is even more electron donating with a Hammett para sigma+constant that has been estimated at –2.3. Chapman, N. B. and Shorter, J., *Correlation Analysis in Chemistry*, Plenum Press, New York, N.Y., page 483–484; Vogel, P., *Carbocation Chemistry*, Elsevier, New York, N.Y. (1985) page 243; Hansch, C., *Comprehensive Medicinal Chemistry*, Pergamon Press, New York, N.Y., 4:235.

The unmasking of a phenol can be carried out in vivo by enzymes. For example, nonspecific esterase is ubiquitous within the cytoplasm of cells and is able to cleave a wide variety of carboxylate esters. Phenolic carbonates and carbamates are degraded by cellular enzymes to yield phenols (Ditter et al., *J. Pharm. Sci.* 57:783 (1968); Ditter et al., *J. Pharm. Sci.* 57:828 (1968); Ditter et al., *J. Pharm. Sci.* 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988)). The unmasking of a phenol can also occur by hydrolysis. For example, a wide variety of carbonate and carbamate groups are known which undergo spontaneous cleavage in solution at kinetically favorable rates (Saari et al., *J. Med. Chem.* 33:97 (1990) and Rattie et al., *J. Pharm. Sci.* 59:1741 (1970)). When A is a substituted benzyl group, cleavage of, for example, a (lower alkyl)—CO—O—, —O—CO—O-(lower alkyl) or —O—CO—NH-(lower alkyl) group in the ortho or para position to give a modified A (A') will trigger heterolytic fission of the C—O bond between modified A (A') and the oxygen of the phosphate. Based on the above considerations the conversion of, for example, an ortho and/or para (lower alkyl)—CO—O—, —O—CO—O-(lower alkyl) or —O—CO—NH-(lower alkyl) group into a hydroxy group will lead to a rate increase of phosphoester fission of at least 7000 fold. If the resulting hydroxy group is ionized to an oxyanion, O⁻, the rate of solvolysis can be further increased about $2 \times 10^{10}$ fold. Based on an intracellular pH of 7 and a pKa of 10 for the phenolic hydroxy group about 0.1% of the hydroxy groups will be ionized under physiological conditions. The net result is that overall a rate increase on the order of $2 \times 10^7$ fold can occur in the heterolytic cleavage of the C—O bond between modified A (A') and the oxygen of the phosphoester following cleavage of an ortho or para acyloxy group in A by nonspecific esterase.

In a preferred embodiment, the prodrugs of the present invention are synthesized by replacing one or more of the hydroxy groups on the phosphorous atoms of the parent drug with a group "A—O—", wherein the group "A" is a substituted benzyl derivative with one or more protected hydroxy groups (e.g. lower alkyl—CO—O—, aryl—CO—O—), —O—CO—O-lower alkyl, —O—CO—O-aryl), —O—CO—NH-lower alkyl and —O—CO—NH-aryl) or protected amine groups in ortho or para positions relative to the phosphoester. The parent drug is liberated following conversion of the protected hydroxy group or protected amino group into the corresponding hydroxy group or amino group, respectively.

Preferably, A is a substituted benzyl group which is further substituted at the benzylic position by a moiety which facilitates cleavage of the phosphoester bond. Suitable substituents at the benzylic position include groups which are capable of stabilizing a carbon cation formed upon cleavage of the phosphoester bond, for example, a lower alkyl group.

More preferably, A is substituted at the benzylic position by a moiety such that cleavage of the phosphoester bond between A or A' and the phosphate oxygen will result in an elimination reaction to form a double bond between the benzylic carbon and the moiety. Suitable moieties are generally bonded to the benzylic position of A with a methylene or methine group having an acidic hydrogen. Upon cleavage of the phosphoester in vivo, A or A' can then undergo an elimination reaction by loss of the phosphate bonded to the benzylic carbon and the acidic hydrogen to form a carbon-carbon double bond at the benzylic position. Alternatively or additionally, a preferred prodrug of the invention is degraded to acyclovir monophosphate or an analog of acyclovir monophosphate by an elimination reaction triggered by the spontaneous or enzymatic unmasking of a strongly electron donating group, such as a hydroxy or amino group at the ortho or para positions of a benzyl group represented by A.

Suitable moieties at the benzylic carbon of the A include those having an electron withdrawing group bonded to the methylene or methine group with the acidic hydrogen (see March, Advanced Organic Chemistry, John Wiley & Sons, third edition (1985) page 884), for example —CHR'—Z, wherein Z is an electron withdrawing group such as —COOR", —COR", —CONH$_2$, —CONHR", —NO$_2$, —SO$_2$R" and —CN.

R' is —H, a lower alkyl group, substituted lower alkyl group, aryl or a substituted aryl.

R" is a lower alkyl group, a substituted lower alkyl group, an aryl group or a substituted aryl group. Preferably, Z is —COOR", wherein R" is methyl, ethyl, n-propyl, iso-propyl, n-butyl, sec-butyl or t-butyl.

Preferably, A is represented by the Structural Formula (V):

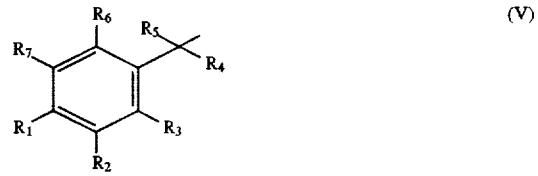

(V)

R$_1$, R$_3$ or R$_6$ are independently selected from the group consisting of —O—CO—R$_8$, —O—CO—OR$_8$, —O—C(O)—NHR$_8$, —O—C(O)—N(R$_8$)$_2$, —NH—CO—R$_8$ and an inert group, with the proviso that at least one of R$_1$, R$_3$ or R$_6$ is not an inert group.

R$_2$ and R$_7$ are hydrogen, an acyloxy group (—O—COR$_8$) or an inert group and may be the same or different.

R$_4$ and R$_5$ are independently selected from the group consisting of hydrogen, a lower alkyl group, a substituted lower alkyl group and a moiety such that cleavage of the phosphoester bond between A or A' and a phosphate oxygen results in an elimination reaction to form a carbon-carbon double bond between the benzylic position of A or A' and the moiety.

R$_8$ is selected from the group consisting of a lower alkyl group, a substituted lower alkyl group, an aryl group, a substituted aryl group and a group such that the resulting ester moiety is degraded to the free phenolic hydroxy group in vivo. Preferably, R$_8$ is selected from the group consisting of methyl, ethyl, n-propyl, iso-propyl, n-butyl, sec-butyl or t-butyl. Other examples include —CHR$_9$—NHR$_{10}$, —CH(OR$_{11}$)—CH$_3$, —CH$_2$—CO—CH$_3$ and —CH$_2$(OR$_{11}$), wherein R$_9$ is the side chain of an amino acid, R$_{10}$ is H or an amine protecting group and R$_{11}$ is H or an alcohol protecting group.

The nature of the labile groups at R$_1$, R$_3$, and R$_6$ determines the rate at which the resulting prodrug is transformed to the parent phosphorus bearing drug. The solubility of the prodrug can be varied by changing the nature of the groups R$_1$–R$_8$. Water solubility can be enhanced by selecting substituents with hydrophilic groups. Alternatively, one can select bulky substituents which disrupt intermolecular forces in the solid phase and lower the prodrug's melting point. Anderson, B., *Physical Chemical Properties of Drugs*, Edited by Yalkoswsky, S., pages 231–266; Marcel Dekker Inc., New York.

In an even more preferred embodiment, the prodrug is represented by the following structural formula:

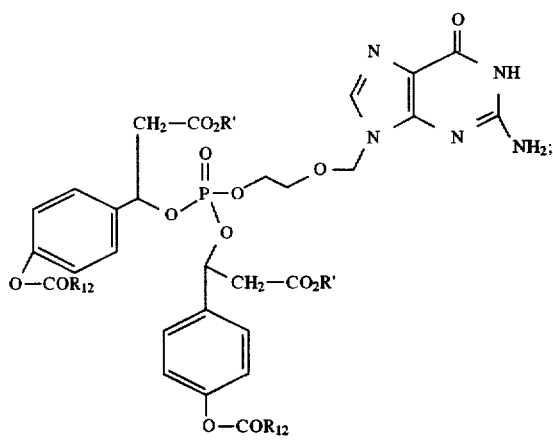

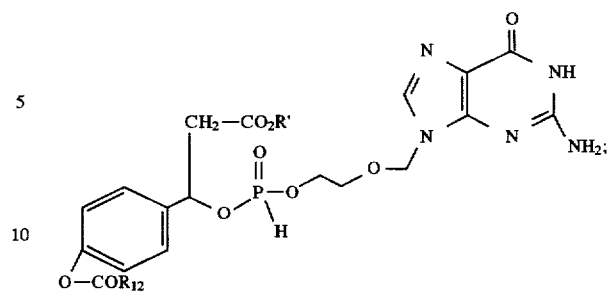

wherein $R_{12}$ and R' are each independently lower alkyl or substituted lower alkyl. $R_{12}$ can also be $CH_3$—CO—$CH_2$—, $CH_3O$—$(CH_2)_2$—O—$(CH_2)_2$—O—$CH_2$—, $CH_3O$—$(CH_2)_2$—O—$CH_2$— and —$OCH_3$. Preferably, $R_{12}$ and R' are each independently selected from the group consisting of methyl, ethyl, n-propyl, iso-propyl, n-butyl, sec-butyl, t-butyl, n-pentyl, n-hexyl, R' is even more preferably methyl.

In another embodiment the prodrug is represented by the following strucutural formula:

wherein $R_{12}$ and R' are each independently lower alkyl or substituted lower alkyl. $R_{12}$ can also be $CH_3$—CO—$CH_2$—, $CH_3O$—$(CH_2)_2$—O—$(CH_2)_2$—O—$CH_2$—, $CH_3O$—$(CH_2)_2$—O—$CH_2$— and —$OCH_3$. Preferably, $R_{12}$ and R' are each independently selected from the group consisting of methyl, ethyl, n-propyl, iso-propyl, n-butyl, sec-butyl, t-butyl, n-pentyl and n-hexyl. R' is more preferably methyl. When $R_{12}$ is —$C(CH_3)_3$ and R' is —$CH_3$, the prodrug is referred to herein as "Prodrug 3".

Without being limited to a particular reaction the mechanism by which the prodrugs are believed to undergo transformation to the parent drug is shown in the scheme below:

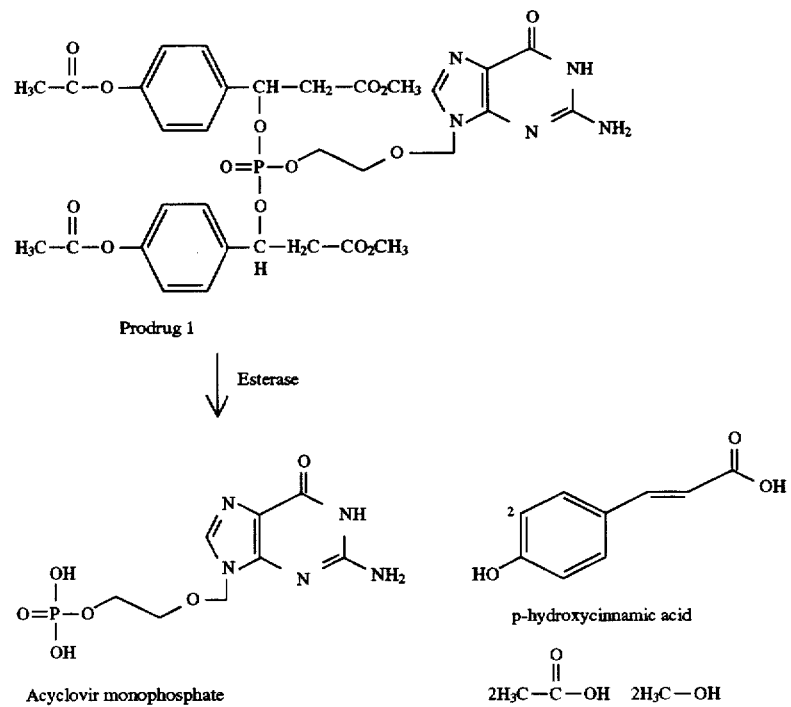

When incubated with pig liver esterase in phosphate buffered $D_2O$, NMR results show that Prodrug 1 is degraded to acyclovir monophosphate and p-hydroxycinnamic, as shown in the Scheme above.

In the above description the term "inert" is used to refer to groups that are substantially nonreactive and to not influence in a major fashion the chemistry of the prodrug metabolism or decay. Examples of inert groups include —H, —OH, —NH$_2$, —NH(lower alkyl), —NH(aryl), lower alkyl, substituted lower alkyl, aryl, substituted aryl, halogen, (lower alkyl)S—, (substituted lower alkyl)S—, (aryl)S—, (substituted aryl)S—, —COO(lower alkyl), (lower alkyl)—O—, (substituted lower alkyl)—O— (e.g. benzyloxy and substituted benzyloxy), —CO-(lower alkyl), —CO-(substituted lower alkyl), —CO-(aryl), —CO-(substituted aryl), —CHO, —CN and —NO$_2$.

As used herein, a "lower alkyl" group can have from 1 to about 20 carbon atoms, preferably 1 to 6 carbon atoms, and can be straight chained, branched or cyclic. In addition, a "lower alkyl" group can have one or more double and/or triple bonds. An "aryl" group includes a carbocyclic aromatic group such as phenyl and naphthyl.

Suitable substituents on a lower alkyl, an aryl group and a benzyl group include inert substituents, as described above.

The prodrugs represented by Structural Formula (I) can be prepared according to procedures described in Examples 3–8. The prodrugs represented by Structural Formula (II) can be prepared according to procedures described in Example 9. Other procedures for preparing the prodrugs of the present invention are described in U.S. Ser. Nos. 07/714,130, 07/537,332 and 08/310,972, the entire teachings of which have been incorporated into this application by reference. It is to be understood that certain modifications in these procedures may be required. For example, changes in the reaction conditions used may be necessary when different A or Y groups are used. Also, the use of protecting groups may be required when A or Y or their chemical intermediates have free functional groups such as hydroxy or amino. The selection of suitable reaction conditions and protecting groups is within the ability of one skilled in the art of organic chemistry.

The prodrugs of the subject application can be used to treat infections in individuals (e.g., humans and animals) caused by various classes of DNA and RNA viruses, including cytomegalovirus, adenovirus (in particular adenovirus 5), rhino virus, Mengo virus, Sinbis virus and vaccinia virus. They are especially active against herpes viruses, including simplex, zoster and varicella, and, in particular, for dermal herpes simplex virus-1 infection. Animals which can treated by the prodrugs of the present invention include veterinary animals, such as dogs, guinea pigs, cats and the like, and farm animals, such as cows, horses, pigs, goats, sheep and the like.

A "therapeutically effective amount" of a prodrug is an amount of prodrug which decreases the duration and/or severity of a viral infection in an individual or animal. Alternatively, a "therapeutically effective amount" comprises an amount of prodrug which lowers the virus titer in an individual or animal with a viral infection or which ameliorates the symptoms and/or discomfort associated with the viral infection. In the case of dermal viral infections, including herpes simplex virus-1, a "therapeutically effective amount" of a prodrug is an amount which decreases lesion number, lesion area and/or virus titer in the skin of an infected individual or animal.

The skilled artisan will be able to determine the precise amount of prodrug to be administered to an individual. The amount of prodrug that is administered to an individual will depend on a number of factors including the general health, size, age and sex of the animal and the route of administration. It will also depend on the degree, severity and type of viral infection. One of ordinary skill in the art will be able to determine the precise dosage according to these and other factors. Typically, between about 0.1 mg/kg body weight per day and about 200 mg/kg body weight per day are administered to the individual or animal.

The prodrug can be administered orally, for example, in capsules, suspensions or tablets. Other modes of parenteral administration which can be used include systemic administration, such as by intramuscular, intravenous, subcutaneous, or intraperitoneal injection. In the case of a virus infection in the skin, for example a dermal herpes simplex virus-1 infection, the prodrug is preferably applied topically directly to the skin lesion which results from the infection.

The prodrug can be administered to the individual or animal in conjunction with an acceptable pharmaceutical carrier as part of a pharmaceutical composition for treating viral infections. Suitable pharmaceutical carriers may contain inert ingredients which do not interact with the prodrug. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

For topical administration for the treatment of viral infections in the skin, the pharmaceutical compositions, in addition to the prodrug, can additionally comprise an inert, non-toxic solvent such as acetone or alcohol in which the prodrug is dissolved, or, preferably, a pharmaceutical carrier suitable for local topical administration in which the prodrug is dissolved or suspended. Examples of pharmaceutically acceptable carriers include, for example, commercially available inert gels, or liquids supplemented with albumin, methyl cellulose or a collagen matrix. Typical of such formulations are ointments, creams and gels. Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration. Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration. Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

The invention is further illustrated by the following examples, which are not intended to be limiting in any way.

EXAMPLE 1

Acyclovir Prodrugs 1 and 2 are More Effective in Reducing Dermal HSV-1 Virus Infection than Acyclovir Formulation The formulation for Prodrugs 1 and 2 contained 5% EL-620 EMULPHOR (polyoxyethylated castor oil) (Rhone Poluenc), 5% CARBOPOL (Carboxypolymethylene, sodium salt) (B.F. Goodrich), 10% ethanol and 1.2% by weight Prodrug 1 (or 1.87% by weight Prodrug 2). The balance of the formulation consisted of water.

EL-620 EMULPHOR and water were mixed and ultrasonicated to give a clear emulsion, to which the ethanol was added. The prodrug was then added, and the mixture was ultrasonicated to give an opalescent emulsion. The sodium carbopol was then added to the emulsion and mixed until to homogeneity.

The placebo was prepared identically to the pharmaceutical compositions except that the prodrugs were omitted.

The pharmaceutical compositions were stored at room temperature.

Animal Inoculation and Subsequent Treatment with Prodrugs 1 and 2

Female Hartley outbred guinea pigs, 400 to 450 grams, were obtained from Charles River Breeding Labs, Wilmington, Mass. Animals were anesthetized with 25 mg/kg ketamine and 5 mg/kg xylazine SQ. Hair on the dorsum from the shoulders to the rump was removed with electric clippers followed by two 5–10 minute applications of a chemical depilatory. A grid of four areas was demarcated with a pen on both sides of the spine at levels corresponding to mid back and rump.

Undiluted HSV-1 virus stock (0.035 ml) was applied to each different area and introduced through the skin at well-spaced sites at ten activations of a six-pronged spring-loaded vaccination instrument (Sterneedle, Pan Ray Division, Ormont Drug, Englewood, N.J.). The day of inoculation is Day 0. Approximately 250 mg of drug or placebo was applied to the areas according to the dosing regimen on Days 1, 2 and 3. Eight guinea pigs were used during the experiments allowing eight comparisons between each drug and its placebo. 5% ZOVIRAX ointment U.S.A. (Acyclovir) applied 4x/day was used as a control.

On Day 4 regrown hair on the dorsum of the guinea pigs was removed with one 3–4 minute application of a chemical depilatory. HSV lesions were counted and Polaroid pictures of the animals' backs were taken. The animals were sacrificed using $CO_2$ gas and the full thickness skin of the back was removed by dissection. The square of the skin from each of the four treatment areas was placed into 15 mls of tissue culture medium with 2% FBS in an ice bath. The samples were then homogenized in a stomacher Lab Blender 80 (Tekmar Co.). Debris was pelleted by centrifugation and the supernatants collected and frozen at −70 C. until assay for infectivity by plaque formation in VERO cells.

Results

The mean and standard deviation for number of lesions, total lesion area and lesion virus titer were computed for each treatment pair. Paired data (drug/vehicle) were evaluated by the Wilcoxon signed-rank test using percent differences between $log_{10}$ derivatives of mean lesions severity at drug-treated sites compared to the vehicle-treated sites. Results for Prodrugs 1 and 2 are shown in Tables 1 and 2, respectively.

Prodrug 1 produced dramatic and significant results in all the efficacy parameters measured, including a 45% reduction in lesion number when compared to its vehicle, a 59% reduction in total lesions area and a 96% reduction in lesion virus titer (all p=0.012). Prodrug 2 produced dramatic and significant results in all the efficacy parameters measured, including a 35% reduction in lesion number when compared to its vehicle, a 57% reduction in total lesions area and a 97% reduction in lesion virus titer (all p=0.012).

U.S. ZOVIRAX produced a non-significant reduction in total lesion area of 12% and a significant reduction in lesion virus titer of 68% (p=0.03) when compared to its placebo. These results for U.S. ZOVIRAX are typical for the compound in this model.

When the results of Prodrugs 1 and 2 were compared with those of U.S. ZOVIRAX using the Mann-Whitney test, Prodrugs 1 and 2 worked significantly better than U.S. ZOVIRAX in all three of the efficacy parameters measured (p=0.0008, 0.0008, 0.001; data not shown).

TABLE 1

| Efficacy of Prodrug 1 Compared with Acyclovir (U.S. ZOVIRAX) | | | | | | |
|---|---|---|---|---|---|---|
|  | Prodrug 1 | % Diff (p) | Plcb B | U.S. ZOVIRAX | % Diff (p) | Placebo |
| Lesion Number | | | | | | |
| mean | 32 | 45[1] | 58 | 55 | 2 | 56 |
| sd | 8 | (.012)[2] | 3 | 4 | (.33) | 3 |
| n | 8 | | 8 | 8 | | 8 |
| median | 32.0 | | 57.5 | 56.0 | | 55.0 |
| Total Lesion Area mm2 | | | | | | |
| mean | 106 | 59 | 259 | 211 | 17 | 253 |
| sd | 24 | (.012) | 37 | 46 | (.07) | 37 |
| n | 8 | | 8 | 8 | | 8 |
| median | 107 | | 271 | 216 | | 249 |
| Titer log (pfu/ml) | | | | | | |
| mean | 3.07 | 96 | 4.49 | 4.09 | 68 | 4.52 |
| sd | .54 | (.012) | .26 | .50 | (.03) | .15 |

TABLE 1-continued

Efficacy of Prodrug 1 Compared with Acyclovir (U.S. ZOVIRAX)

|        | Pro-drug 1 | % Diff (p) | Plcb B | U.S. ZOVIRAX | % Diff (p) | Placebo |
|--------|------------|------------|--------|--------------|------------|---------|
| n      | 8          |            | 8      | 8            |            | 8       |
| median | 3.17       |            | 4.55   | 3.98         |            | 4.44    |

[1]Percent differences between mean lesion severity at drug-treated sites compared to the vehicle-treated sites are shown. A positive value indicates a reduction in lesion severity for test compound.
[2]Day 0 is the day of infection. Prodrug 1 cream, prepared as described in Example 1, was used 2x/day on Days 1, 2 and 3; U.S. Zovirax was used 4x/day on Days 1, 2 and 3.
[3]For statistical analysis, paired data were evaluated by the Wilcoxon signed rank test, utilizing the percent differences between $\log_{10}$ derivatives of the drug and placebo results.

TABLE 2

Efficacy of Prodrug 2 Compared with Acyclovir (U.S. ZOVIRAX)

|                         | Pro-drug 2 | % Diff (p) | Placebo | U.S. ZOVIRAX | % Diff (p) | Placebo |
|-------------------------|------------|------------|---------|--------------|------------|---------|
| Lesion Number       |            |            |         |              |            |         |
| mean                    | 37         | 35[1]      | 57      | 56           | 0          | 56      |
| sd                      | 12         | (.012)[2]  | 4       | 4            | (.87)      | 4       |
| n                       | 8          |            | 8       | 8            |            | 8       |
| median                  | 36.0       |            | 57.5    | 57.5         |            | 57.5    |
| Total Lesion Area mm2 |          |            |         |              |            |         |
| mean                    | 110        | 57         | 255     | 192          | 25         | 257     |
| sd                      | 46         | (.012)     | 42      | 46           | (.02)      | 53      |
| n                       | 8          |            | 8       | 8            |            | 8       |
| median                  | 109        |            | 254     | 206          |            | 262     |
| Titer log (pfu/ml)  |            |            |         |              |            |         |
| mean                    | 2.87       | 97         | 4.38    | 3.85         | 61         | 4.26    |
| sd                      | .71        | (.012)     | .24     | .52          | (.02)      | .39     |
| n                       | 8          |            | 8       | 8            |            | 8       |
| median                  | 3.12       |            | 4.41    | 3.97         |            | 4.37    |

[1]Percent differences between mean lesion severity at drug-treated sites compared to the vehicle-treated sites are shown. A positive value indicates a reduction in lesion severity for test compound.
[2]Day 0 is the day of infection. Prodrug 2 cream, prepared as described in Example 1, was used 2x/day on Days 1, 2 and 3; U.S. Zovirax was used 4x/day on Days 1, 2 and 3.
[3]For statistical analysis, paired data were evaluated by the Wilcoxon signed rank test, utilizing the percent differences between $\log_{10}$ derivatives of the drug and placebo results.

EXAMPLE 2

Prodrugs 1-3 are Active in vivo Against HSV-1 and Acyclovir Resistant HSV-1

Introduction

The following test were carried out essentially as described by Sidwell and Huffman (Sidwell, et al., *App. Microbiol.*, 22:797-801 (1971)), and was used in the reports on the in vitro antiviral activity of ribavirin (Sidwell, et al. *Science*, 177:705-706 (1972); Huffman, et al., Antimicrob. Ag. Chemother., 3:235-241 (1973)).

Viruses

Herpes type 1 virus (HSV-1), BWVL#10186, is a thymidine kinase positive (TK$^+$) human clinical isolate provided by Dr. M. Nixon Ellis, Burroughs Wellcome Co. (Research Triangle Park, N.C.). The BWVL#10168 strain of HSV-1 is a TK- patient isolate (resistant partner to 10186) that was also provided by Dr. Ellis. Both strains were prepared in Vero cells, ampuled, and frozen at $-80°$ C. Antiviral testing was performed in Vero cells.

Cells and Media

The following cells and media were used with both strains of virus:

Vero (continuously passaged African green monkey kidney) was obtained from the American Type Culture Collection (ATCC) (Rockville, Md.). Growth medium was Medium 199, 5% FBS and 0.1% NaHCO$_3$. Test medium was Eagle's minimum essential medium with non-essential amino acids (MEM), with 2% FBS, 0.18% NaHCO$_3$ and 50 μg gentamicin/ml. The growth medium contained no antibiotics.

Preparation of Compounds for Testing

Compounds were weighed and a sufficient amount added to DMSO (American Type Culture Collection, Rockville, Md.) to prepare a solution at 20 mg/ml.

Antiviral Testing Procedure

Cells were seeded to 96-well flat-bottomed tissue culture plates (Corning Glass Works, Corning, N.Y.), 0.2 ml/well, at the proper cell concentration, and incubated overnight at 37° C. in order to establish cell monolayers. The growth medium was decanted and the various dilutions of test compound were added to each well (4 wells/dilution, 0.1 ml/well). Compound diluent medium was added to cell and virus control wells (0.1 ml/well). Virus, diluted in test medium, was added to compound test wells (3 wells/dilution of compound) and to virus control wells at 0.1 ml/well. Virus was added approximately 5 minutes after compound. Test medium without virus was added to all toxicity control wells (1 well/dilution of each test compound) and to cell control wells at 0.1 ml/well. The plates were sealed with plastic wrap (SARAN™) and incubated at 37° C. in a humidified incubator with 5% $CO_2$, 95% air atmosphere until virus control had adequate cytopathic effect (CPE) readings. This was usually achieved after 72 hours. Cells were then examined microscopically for CPE, this being scored from 0 (normal cells) to 4 (maximal, 100%, CPE). The cells in the toxicity control wells were observed microscopically for morphologic changes attributed to cytotoxicity. This cytotoxicity was graded as: T (assigned 100% toxicity), PVH (assigned 80% cytotoxicity), $P_H$ (assigned 60% cytotoxicity), P (assigned 40% cytotoxicity), $P_{SI}$ (assigned 20% cytotoxicity), and 0 (normal cells). The 50% effective dose (ED50) and 50% cytotoxic dose (CD50) were calculated by regression analysis of the virus CPE data and the toxicity control data, respectively.

A known active substance, acyclovir, was run in the same manner as above for each batch of compounds tested.

Prodrug 1, Prodrug 2, Prodrug 3 and acyclovir were tested for activity against the $TK^+$ and (acyclovir resistance strain) strains of HSV-1 according to the procedures described above. All three prodrugs had activities that were of the same order of magnitude as acyclovir as against $TK^+$, as shown in Table 3. Against $TK^-$, Prodrugs 1 and 2 were about 2× and about 5× more active, respectively, than acyclovir, also shown in Table 3.

TABLE 3

In Vitro Antiviral Activity of Prodrugs 1-3

| Virus | $TK^+$ HSV 1 $ED_{50}$ micromolar | $TK^-$ HSV 1 $ED_{50}$ micromolar | $CD_{50}$ μg/ml |
|---|---|---|---|
| Drug | | | |
| Acyclovir | 1.4 | 35 | >100 |
| Prodrug 1 | 4.6 | 17 | >100 |
| Prodrug 2 | 6.3 | 7.5 | >100 |
| Prodrug 3 | 5.5 | 37 | >100 |

EXAMPLE 3

Synthesis of Methyl (4-Hydroxybenzoyl)acetate

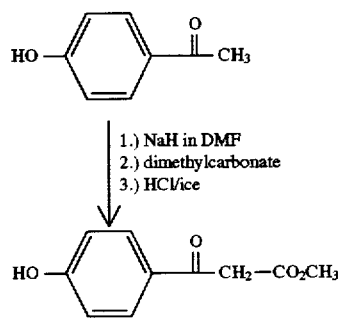

Materials:
1) 4-Hydroxyacetophenone Aldrich 27,856-3, 99%
2) Sodium hydride Aldrich 19,923-0, 60% dispersion in mineral oil, F.W. 24.00
3) Dimethylcarbonate Aldrich D15,292-7
4) Dimethylformamide (anhydrous) Fluka 40248
5) Petroleum ether (anhydrous) Aldrich 30,031-4

| Reagent | $HO-C_6H_4-COCH_3$ | NaH | $(CH_3O)_2CO$ |
|---|---|---|---|
| F.W. | 136.15 | 24.00 | 90.08 |
| d | | | 1.069 |
| gm | 50.4 | 74 | 167 |
| ml | | | 156 |
| mo | 0.37 | 1.85 | 1.85 |
| eqv. | 1 | 5 | 5 |

Apparatus:
3 L, 3 neck round bottom flask, mechanical stirrer, addition funnel thermometer, cooling bath, Argon bubbler.

Procedure:
Sodium hydride was suspended under anhydrous argon in petroleum ether (250 ml), left to settle down and the solvent was removed under argon. The procedure was repeated with another portion (250 ml) of petroleum ether. 250 ml of anhydrous DMF was added.

A solution of 4'-hydroxyacetophenone in 250 ml dimethylformamide (DMF) was added drop wise to the suspension of NaH in 250 ml (DMF) over a 1.5 hour period and the temperature was kept below 32° C. by intermittent cooling with ice an bath. When the addition was completed, the reaction mixture was stirred for 15 minutes until the gas evolution had subsided and the temperature dropped to 28° C. Dimethylcarbonate was added drop wise over 1 hour and the temperature was maintained below 35° C.

The reaction mixture was stirred at room temperature under argon for 36 hours.

Work up:
The reaction mixture was cooled with an ice bath. Methanol (125 ml) followed by water (20 ml) was added drop wise to the reaction mixture with stirring. The temperature increased to 40° C. and a vigorous gas evolution was observed. When the gas evolution ceased the reaction mixture was acidified with concentrated HCl (170 ml) to pH 2.5.

The reaction mixture was poured into ice (1.5 L volume) and extracted with ethylacetate (4×250 ml). Combined ethylacetate extracts were washed with water (1×200 ml), 5% citric acid (2×200 ml), 5% $NaHCO_3$ (2×200 ml), water (2×200 ml), dried over $Na_2SO_4$ and concentrated on rotary evaporator.

The residual oil was crystallized from toluene/hexane. Yield 63 gm—89%.

The reaction and work up were monitored by TLC in 40% ethylacetate in hexane.

EXAMPLE 4

Synthesis of Methyl (4-Acetoxybenzoyl)acetate

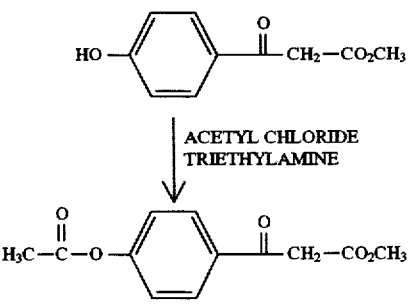

Materials:
1) Methyl (4-Hydroxybenzoyl)acetate F.W. 136.15

2) Acetyl chloride Aldrich 23,206-3 F.W. 78.50
3) Triethylamine Aldrich 13,206-3

| Reagent | HO—C$_6$H$_4$—COCH$_3$ | CH$_3$COCl | N(C$_2$H$_5$)$_3$ |
|---|---|---|---|
| F.W. | 194.19 | 78.50 | 101.19 |
| d | | 1.104 | 0.726 |
| gm | 20 | 8.9 | 11.4 |
| ml | | 8.06 | 15.8 |
| mo | 0.103 | 0.113 | 0.113 |
| eqv. | 1 | 1.1 | 1.1 |

To a stirred and cooled solution of methyl (4-hydroxybenzoyl)acetate in 150 ml anhydrous chloroform and triethylamine a solution of acetyl chloride in 20 ml chloroform was added drop wise over 15 minutes.

When the addition was completed, the ice bath was removed and the reaction mixture was stirred at room temperature for 2 hours.

The reaction was monitored by TLC in 40% ethylacetate in hexane.
Work up:

The reaction mixture was washed with water (3×100 ml), 5% NaHCO$_3$ (3×100 ml), water (1×100 ml), dried over Na$_2$SO$_4$ and the solvent removed on rotary evaporator. The oily residue was dissolved in petroleum ether (100 ml) and cooled with dry ice/acetone to crystallize. The crystals were filtered and washed with petroleum ether to give 24 gm of a white powder. Yield 100%.

The pivaloyl derivative was synthesized in the same manner by using trimethylacetyl chloride.

EXAMPLE 5

Synthesis of Methyl 3-hydroxy-3-(4-Acetoxyphenyl) propanoate

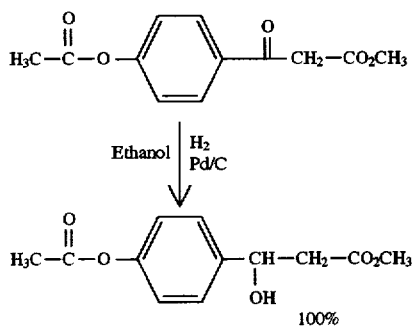

A Parr apparatus was charged with methyl (4-acetoxybenzoyl)acetate, ethanol and a catalytic amount of 10% Palladium on activated carbon. The mixture was reacted for six hours with stirring under a H$_2$ atmosphere at 200 psi.

EXAMPLE 6

Synthesis of Pixyl Acyclovir

[9-(Hydroxyethoxymethyl)-2—N-(9-phenylxanthen-9-yl)-guanine]

Ref: Welch, C. J., et al., "The Chemical Synthesis and Antiviral Properties of an Acyclovir-phospholipid Conjugate" Acta Chem. Scand. B 39:47 (1985).

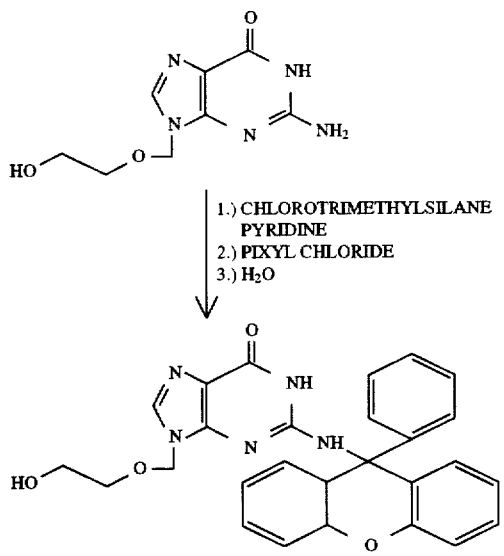

Materials:
1) Acyclovir
2) Trimethylchlorosilane
3) 9-Chloro-9-phenylxanthene
4) Pyridine

| Reagent | 1 | 2 | 3 |
|---|---|---|---|
| F.W. | 225 | 108.64 | 292.77 |
| d | | 0.856 | |
| gm | 40 | 77.35 | 62.5 |
| ml | | 90.4 | |
| mo | 0.178 | 0.712 | 0.214 |
| eqv. | 1 | 4 | 1.2 |

A suspension of acyclovir in dry pyridine (10 ml/mmol of substrate, 1.8 L) was treated with trimethylchlorosilane with stirring at room temperature. When a reaction mixture formed a clear solution, 9-chloro-9 phenylxanthene was added and the reaction mixture was stirred for 30 minutes at room temperature under argon.

The mixture was poured into a solution of 5% sodium bicarbonate (1.5 L) and stirred for 15 minutes, then extracted with chloroform (3×300 ml). The solvent was removed in vacuum and the residue was dissolved in pyridine (300 ml) and methanol (500 ml). After 30 minutes the reaction mixture was evaporated to dryness, dissolved in methylene chloride (100 ml) and precipitated with diethyl ether to obtain pure pixyl acyclovir 83.3 gm in 97% yield. TLC in chloroform/methanol/water (5:1:0.1).

EXAMPLE 7

Synthesis of Prodrug 1

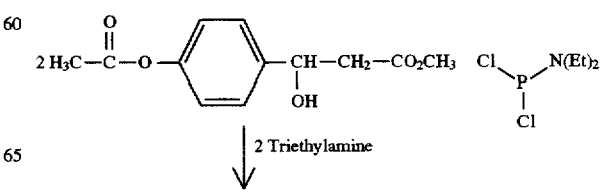

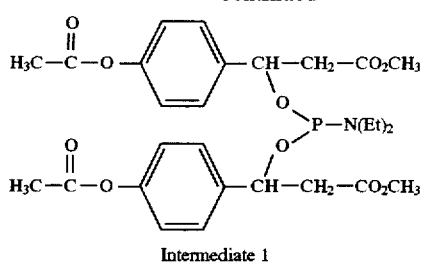

Intermediate 1

Materials:

1) Methyl 3-(4-acetoxyphenyl)-3-hydroxypropionate (acetoxy alcohol), anhydrous

2) Diethylphosphoramidous dichloride Aldrich 36,289-1

3) Triethylamine, Aldrich 13,206-3

| Reagent | Acetoxy Alcohol | Diethyl Phosphoroamidous Dichloride | Triethyl Amine |
|---|---|---|---|
| F.W | 238.23 | 174.01 | 101.19 |
| d |  | 1.196 | 0.726 |
| gm | 15 | 5.48 | 6.4 |
| ml |  | 4.58 | 8.8 |
| mol | 0.063 | 0.0315 | 0.063 |
| eqv | 2 | 1 | 2 |

Apparatus:

500 ml round bottom flask, magnetic stirrer, argon bubbler.

To a cooled (dry ice/acetone) solution of acetoxy alcohol and triethylamine in anhydrous tetrahydrofuran (THF) (100 ml) was added at once under argon, diethylphosphoroamidous dichloride. After 30 minutes the ice bath was removed and reaction mixture was stirred overnight under argon at room temperature.

The reaction mixture was filtered under argon from triethylamine hydrochloride and the precipitate was washed with anhydrous THF (2×50 ml) and the filtrate was concentrated on rotary evaporator to dryness to give a colorless oil in quantitative yield.

The reaction was monitored by TLC in 40% ethylacetate in hexane.

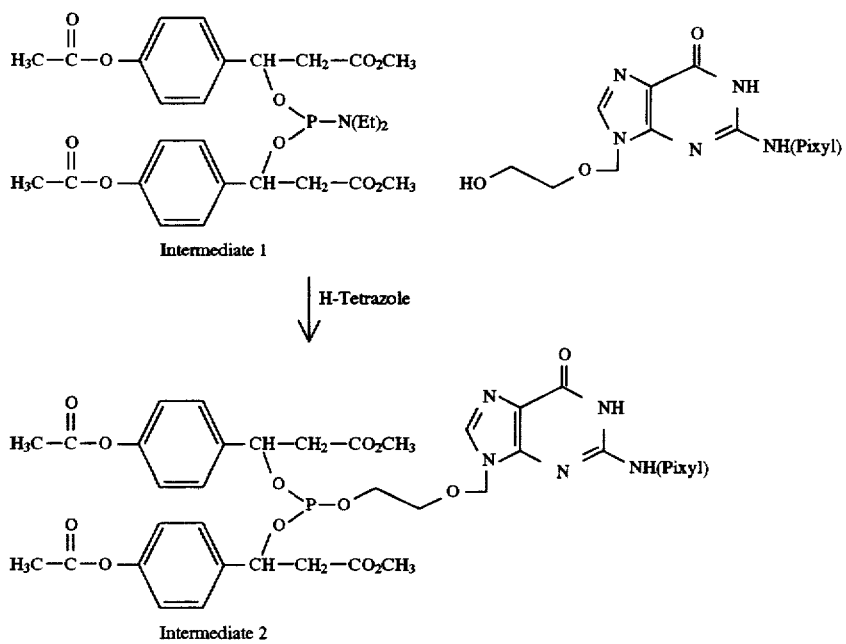

Materials:

1) Pixyl acyclovir (anhydrous)

2) Intermediate 1

3) 1H-Tetrazole (anhydrous)

| Reagent | 1 | 2 | 3 |
|---|---|---|---|
| F.W | 481.27 | 577.54 | 70.0 |
| d |  |  |  |
| gm | 9.5 | 18 | 2.76 |
| ml |  |  |  |

| Reagent | 1 | 2 | 3 |
|---------|---|---|---|
| mol | 0.0197 | 0.0315 | 0.0394 |
| eqv | 1 | 1.6 | 2 |

Intermediate 1 was added at once to a stirred solution of pixyl acyclovir and 1H-tetrazole in anhydrous DMF (100 ml) under argon. The reaction mixture was stirred at room temperature for 2 hours to yield Intermediate 2.

The reaction was monitored by TLC in $CHCl_3/CH_3OH/H_2O$ 5:1:0.1. The samples for TLC were diluted with ethylacetate and washed with water, to remove the DMF, which splits the spots.

Oxidation:

taining Intermediate 2 in 100 ml DMF and stirred for 10 minutes. The cooling bath as removed and the reaction was left for 30 minutes at room temperature.

A 10% solution of $Na_2SO_3$ (300 ml) was added and the mixture was stirred for 10 minutes, which caused formation of a white gummy precipitate. The mixture was extracted with ethyl acetate (2×350 ml). Combined ethyl acetate extracts were washed with water (2×300 ml) and concentrated under vacuum. The residue was mixed with toluene (300 ml) and evaporated to dryness.

Deblocking:

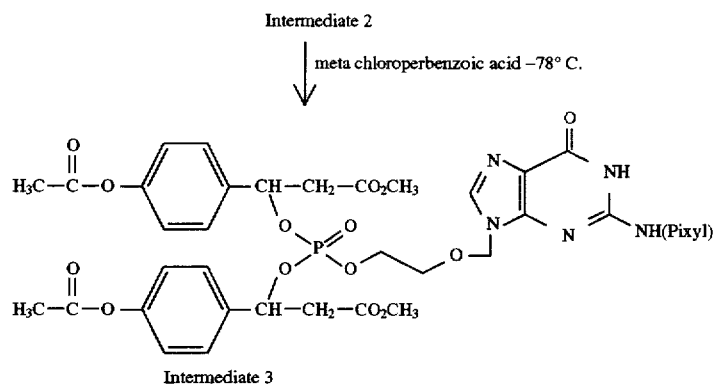

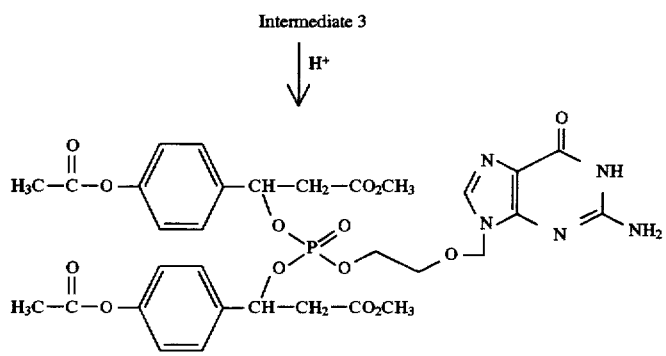

| Reagent | 3-Chloroperbenzoic acid, 57–86%, Aldrich 27,303-1 |
|---------|---|
| F.W. | 172.6 |
| gm | 6.9 |
| mol | 0.2–0.3 |

3-Chloroperbenzoic acid dissolved in 10 ml DMF was added to a cooled (dry ice/acetone) reaction mixture con- 2-Mesitylenesulfonic acid dihydrate, 97% Aldrich 12,963.1.

The crude product after oxidation was dissolved in $CHCl_3$ (300 ml) and $CH_3OH$ (100 ml) and to the clear solution was added 2-mesitylenesulfonic acid (F.W. 263.3, 0.01 mol, 2.6 gm, 0.5 eqv.). The reaction was monitored by TLC in chloroform/methanol/water (5:1:0.1). Reaction time was 4 hours. When the deblocking was complete, the solvents were evaporated on vacuum. The residual oil was dissolved in chloroform (500 ml) and washed with 5% sodium carbonate (2×200 ml), water (2×200 ml), dried over sodium sulfate and the chloroform was removed under vacuum.

The crude product was purified on a silica gel column (300 ml dry volume), with mobile phase chloroform/methanol 20:1 (v/v).

Fractions of 100 ml each were collected. Fractions #4 to #18 were combined and the solvent was removed under vacuum to give 10.1 gm of product in 67% yield. (F.W. 761.4).

EXAMPLE 8

Synthesis of Prodrug 2

The pivaloyl acyclovir prodrug was synthesized in the same manner in 53% yield in the manner described in Examples 3–7 except that pivaloyl chloride (trimethylacetyl chloride) was used in place of acetyl chloride in Example 4. The final product was isolated by crystallization from:

1) acetone/water
2) diethyl ether/petroleum ether.

EXAMPLE 9

Synthesis of Prodrug 3

Prodrug 3 was synthesized using procedures identical to those disclosed in Examples 3–7 except that only one equivalent of the acetoxy alcohol was reacted in Example 7 and the oxidation step in Example 7 may be omitted.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A compound represented by a structural formula selected from the group consisting of:

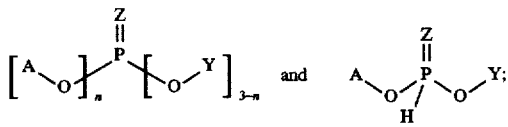

wherein

Z is oxygen or sulfur;

n is 1 or 2; and

Y, together with a hydroxy group, is 9-[(2-hydroxyethoxy)methyl] guanine or an analog of 9-[(2-hydroxyethoxy)methyl] guanine; and A is a substituted benzyl group with one or more protected hydroxy or protected amine groups in the ortho or para positions, relative to the phosphoester, which are converted in vivo to a hydroxy or amino group.

2. The compound of claim 1 wherein Z and X are oxygen, $R_a$ is —OH and $R_b$ is —NH$_2$.

3. The compound of claim 2 wherein $R_c$, $R_d$ and $R_e$ are each —H.

4. The prodrug of claim 3 wherein the one or more groups in the para or ortho positions relative to the phosphoester are selected from the group consisting of $R_8$—O—CO—O—, $R_8$NH—CO—O—, and $R_8$CO—O—, wherein $R_8$ is selected from the group consisting of lower alkyl, substituted lower alkyl, aryl and substituted aryl.

5. The compound of claim 4 wherein the benzyl group is α-substituted with a moiety such that cleavage of the phosphoester bond between A and a phosphate oxygen results in an elimination reaction to form a carbon-carbon double bond between the α-carbon and the moiety.

6. The compound of claim 4 wherein the one or more groups in the para or ortho positions relative to the phosphoester are (lower alkyl)CO—O—.

7. The prodrug of claim 3 wherein A is of the formula:

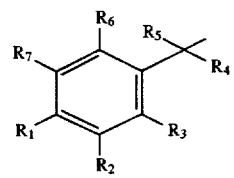

wherein:

$R_1$, $R_3$ or $R_6$ are independently selected from the group consisting of —O—CO—$R_8$, —O—CO—O$R_8$, —O—C(O)—NHR$_8$, —O—C(O)—N(R$_8$)$_2$, —NH—CO—$R_8$ and an inert group, with the proviso that at least one of $R_1$, $R_3$ or $R_6$ is not an inert group;

$R_2$ and $R_7$ are hydrogen, —O—CO—$R_8$, or an inert group and may be the same or different;

$R_4$ and $R_5$ are independently selected from the group consisting of hydrogen, a lower alkyl group, a substituted lower alkyl group and a moiety such that cleavage of the phosphoester bond between A and a phosphate oxygen results in an elimination reaction to form a carbon-carbon double bond between the benzylic position of A and the moiety; and $R_8$ is selected from the group consisting of a lower alkyl group, a substituted lower alkyl group, an aryl group, a substituted aryl group, and a group such that the resulting ester moiety is degraded to the free phenolic hydroxy group in vivo.

8. The compound of claim 7 wherein at least one of $R_1$, $R_3$ or $R_6$ is a (—O—CO—$R_8$) group.

9. The compound of claim 8 wherein the moiety that results in an elimination reaction is —CH$_2$COOR", —CH$_2$COR", —CH$_2$CONH$_2$, —CH$_2$CONHR", —CH$_2$NO$_2$, —CH$_2$SO$_2$R" and —CH$_2$CN, wherein R" is selected from the group consisting of lower alkyl, substituted lower alkyl, aryl and substituted aryl.

10. The compound of claim 9 wherein $R_4$ is a —CH$_2$—CO$_2$—R".

11. The compound of claim 10 wherein R" is selected from the group consisting of methyl, ethyl n-propyl, iso-isopropyl, n-butyl, sec-butyl, t-butyl.

12. The compound of claim 11 wherein $R_1$ is a —O—CO—$R_8$.

13. The compound of claim 12 wherein $R_8$ is selected from the group consisting of methyl, ethyl n-propyl, iso-isopropyl, n-butyl, sec-butyl, t-butyl, n-pentyl, n-hexyl, CH$_3$—CO—CH$_2$—, CH$_3$O—(CH$_2$)$_2$—O—(CH$_2$)$_2$—O—CH$_2$—, CH$_3$O—(CH$_2$)$_2$—O—CH$_2$— and —OCH$_3$.

14. A compound represented by the following structural formula:

15. A compound represented by the following structural formula:

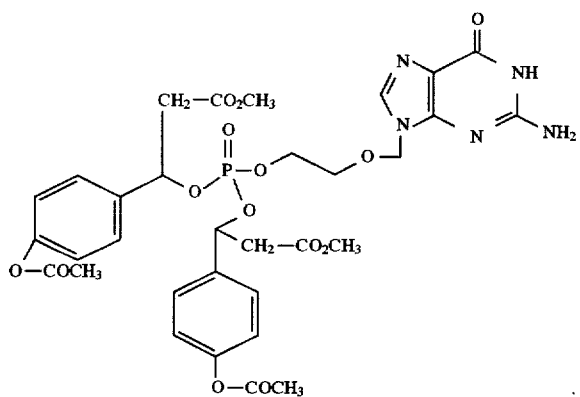

16. A compound represented by a structural formula selected from the group consisting of:

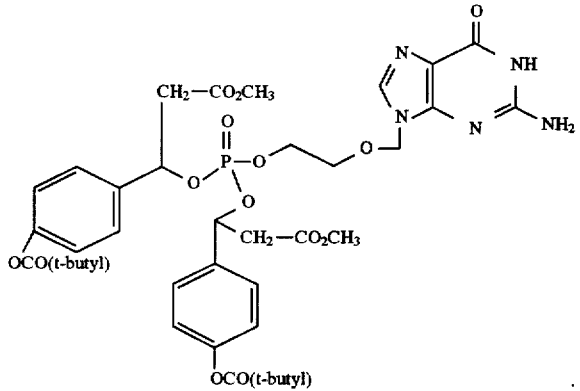

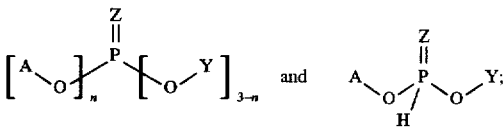

wherein:
Z is oxygen or sulfur;
n is 1 or 2;
A is a substituted benzyl group with one or more protected hydroxy or protected amine groups in the ortho or para positions, relative to the phosphoester, which are converted in vivo to a hydroxy or amino group;
Y is represented by the following structural formula:

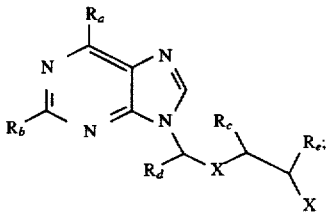

wherein:
X is sulphur, nitrogen or oxygen;
$R_a$ is hydrogen, halogen, hydroxy, (lower alkyl)—O—, azide, thio, (lower alkyl)thio, amino, (lower alkyl) amino or di(lower alkyl)amino;
$R_b$ is hydrogen, halogen, (lower alkyl)thio, (lower alkyl) —CO—NH—, amino or azide;
$R_c$ is hydrogen, lower alkyl, substituted lower alkyl, aryl and substituted aryl;
$R_d$ is hydrogen or lower alkyl; and
$R_e$ is hydrogen, lower alkyl, substituted lower alkyl, aryl, substituted aryl, (lower alkyl)O—, (substituted lower alkyl)O—, aryloxy and substituted aryloxy.

* * * * *